(12) United States Patent
Abelson et al.

(10) Patent No.: US 6,465,506 B2
(45) Date of Patent: Oct. 15, 2002

(54) INSTILLATION TECHNIQUES FOR OPHTHALMIC AGENTS TO ENHANCE TREATMENT EFFECT

(75) Inventors: Mark B. Abelson, Andover, MA (US); George W. Ousler, III, Andover, MA (US)

(73) Assignee: Ophthalmic Research Associates, Inc., N. Andover, MA (US)

( * ) Notice: Subject to any disclaimer, the term of this patent is extended or adjusted under 35 U.S.C. 154(b) by 0 days.

(21) Appl. No.: 10/080,873

(22) Filed: Feb. 22, 2002

(65) Prior Publication Data

US 2002/0115587 A1 Aug. 22, 2002

Related U.S. Application Data

(60) Provisional application No. 60/270,741, filed on Feb. 22, 2001.

(51) Int. Cl.$^7$ ............................................. A61K 31/415
(52) U.S. Cl. ....................................... 514/397; 514/912
(58) Field of Search ................................. 514/397, 912

(56) References Cited

U.S. PATENT DOCUMENTS 6,056,950 A * 5/2000 Saettone et al. ......... 424/78.04

* cited by examiner

*Primary Examiner*—Zohreh Fay
(74) *Attorney, Agent, or Firm*—Mintz, Levin, Cohn, Ferris, Glovsky and Popeo, P.C.

(57) ABSTRACT

The present invention provides methods for instilling an ophthalmic agent. One embodiment of a method according to the invention includes causing a patient to refrain from blinking for at least a specified period of time so as to effect the substantial break down of the patient's tear film covering the patient's eye and instilling an ophthalmic agent to the patient's eye.

8 Claims, No Drawings

INSTILLATION TECHNIQUES FOR OPHTHALMIC AGENTS TO ENHANCE TREATMENT EFFECT

CROSS-REFERENCE TO RELATED APPLICATIONS

This application claims benefit of U.S. Provisional Application No. 60/270,741, filed Feb. 22, 2001, the entire disclosure of which is incorporated herein by reference.

FIELD OF THE INVENTION

The invention relates to a process for instilling an ophthalmic agent that enhances the efficacy of the ophthalmic agent.

BACKGROUND OF THE INVENTION

The tear film, which covers the ocular surface, is a complex fluid secreted by several different orbital glands and ocular surface epithelial cells. The main functions of this film are to protect and maintain the surface of the eye. Examples of the environmental stimuli responsible for challenging the ocular surface include, but are not limited to, desiccation, bright light, cold, mechanical stimulation, physical injury, noxious chemicals, various foreign bodies such as pollen, and bacterial, viral, and parasitic infection. The tear film maintains the health of the ocular surface by providing optimal conditions, such as proper electrolyte composition, pH level, protein composition, and nutrient levels in the tears.

As a response to these external challenges and internal requirements, there is exquisite control of tear volume, composition, and structure of the tear film. The tear film consists of three layers, a lipid, aqueous, and mucous layer. The lipid, or outermost layer (closest to the environment), consists mainly of hydrophobic wax monoesters and sterol esters, and is responsible for preventing evaporation in the open eye. The aqueous, or middle layer, consists mainly of tear proteins, electrolytes, and water, to protect against microbial agents and bacteria, and supply nutrients such as dissolved oxygen to the ocular surface. The mucous, or innermost layer (closest to the eye), consists mainly of hydrophilic mucin which stabilizes the tear film and allows it to spread over the ocular surface. This layer also protects the ocular surface from the environment by preventing microbial invasion, physical and chemical trauma, and desiccation of the eye.

The three layer tear film structure remains intact for a certain period of time before it begins to break apart or rupture, exposing the ocular surface. This mechanism is known as the tear film break-up time (TBUT) and is defined as the interval between the last complete blink and the first appearance of a dry spot formation or disruption in the tear film. Once tear film break up occurs, blinking is necessary to replenish this complex fluid. Therefore, anything that interferes with normal blinking can lead to the minimization and/or absence of the tear film and drying of the ocular surface.

A common challenge associated with the instillation of any ophthalmic agent is its ability to penetrate the tear film at its highest concentration to ensure maximum treatment effect. The barrier function of the tear film makes it difficult for an ophthalmic agent to be effective by restricting the product's interaction with target receptors of the ocular surface. Additionally, the tear film composition is responsible for diluting ophthalmic agents, resulting in further reduced efficacy.

Therefore, an improved instillation technique by which any ophthalmic agent can overcome the barrier and dilution factors of the tear film to enhance treatment effect is necessary.

SUMMARY OF THE INVENTION

The present invention provides a novel instillation technique that enhances the efficacy of ophthalmic agents as they are delivered to the surface of the eye. This technique requires patients to refrain from blinking for a period of time prior to instilling an ophthalmic agent. Consequently, the tear film breaks up (becomes minimized or absent), allowing the vehicle and active components of an ophthalmic agent to interact with the surface of the eye more quickly and at a higher concentration. By overcoming the barrier and dilution factors of the tear film, an ophthalmic agent's rate of onset of action and potency may be improved.

Thus, one version of the invention provides a method for instilling an ophthalmic agent. The method includes causing a patient to refrain from blinking for at least a period of time so as to initiate the break down of the patient's tear film covering the patient's eye and thereafter instilling an ophthalmic agent to the patient's eye.

DETAILED DESCRIPTION OF THE INVENTION

Any topical ophthalmic agent including, but not limited to, mydriatics and cycloplegics, antimicrobial therapy, ocular anti-inflammatory products, anesthetic products, products for treatment of glaucoma, products for dry eye, ocular decongestants, hyperosmolar products, diagnostic products, and viscoelastic materials used in ophthalmology can be instilled using the method of the invention. When this technique is practiced, the following instructions should be carried out by a(n):

1) Patient (for self-instillation);
2) Medical professional (including, but not limited to, an ophthalmologist, optometrist, or ophthalmic technician);
3) Individual assisting the patient (such as, but not limited to, a caretaker, family member, or friend).

Prior to the instillation of an ophthalmic agent, the instiller (as identified above) waits until the tear film begins to break apart, exposing the surface of the eye. The instiller accomplishes tear film break up by having the patient open his or her eye and stare for a period of time, without blinking. The tear film break up time can be determined by a medical professional (such as, but not limited to, an ophthalmologist or optometrist) or the patient based on ocular discomfort associated with the disruption of a tear film. Once the tear film has broken up, the ophthalmic agent should be delivered to surface of the eye. The patient can then blink freely. Clinical experience indicates that tear film break up times in the human population typically range between about 2 seconds to about 30 seconds.

This mode of instillation maximizes the penetration and binding of any ophthalmic agent not only into structures of the ocular surface (such as, but not limited to, the conjunctiva, sclera, and extra-ocular muscles) but also the structures of the intra-ocular space (such as, but not limited to, the retina, vitreous, lens, and intra-ocular muscles).

One embodiment of the present invention provides a method for instillation of an ophthalmic agent. One can include a description of the method on a package insert associated with, and/or on a container for, an ophthalmic agent. This description can indicate that the method of the present invention is the proper instillation technique to enhance treatment effect. Embodiments of the invention provide improved efficacy in a variety of circumstances including:

1) Obtaining any claim with the United States Food and Drug Administration (or any equivalent foreign regulatory body) for any ophthalmic agent;
2) Assisting in the regulatory approval process of any ophthalmic agent;
3) Designing a clinical trial (Phase I, II, III, or IV) to evaluate any ophthalmic agent;
4) Acquiring information to be used in any marketing/advertisement materials or scientific publications (such as, but not limited to, abstracts, posters, and journals).

EXAMPLE

The following study examines the efficacy of pilocarpine, 1% in constricting the pupil and tropicamide, 1% in dilating the pupil when instilled before and after TBUT. Baseline pupil diameters were determined in 12 normal eyes using a digital imaging system (and controlling illumination). Six (6) of the eyes were dosed with 30 $\mu$L of pilocarpine and 6 with 30 $\mu$L of tropicamide, all before TBUT. Pupil diameter was measured every minute for 30 minutes after instillation. One day later, the same procedures were repeated in the same eyes, except that the subjects were instructed to stare without blinking ($\geq$6 seconds) before the ophthalmic agents were instilled.

Pilocarpine treated eyes yielded a mean decrease of 2.44 units from the baseline in pupil diameter at 30 minutes when instillation occurred after TBUT and 1.12 units when it occurred before TBUT (p<0.05). Over the 30 minute period, instillation after TBUT resulted in greater pupil constriction (by 29.44%). Tropicamide treated eyes yielded a mean result of 2.12 units from baseline in pupil diameter at 30 minutes when instillation occurred after TBUT and 1.28 units when it occurred before TBUT (p<0.05). Over the 30 minute period, instillation after TBUT resulted in greater pupil dilation (by 36.21%).

The data suggest that by allowing TBUT to occur before drop instillation, the efficacy of pilocarpine (1%) and tropicamide (1%) in constricting and dilating the pupil, respectively, is significantly improved. By overcoming the barrier function and dilution factor of the tear film, ophthalmic agents can be more effective.

Having thus described illustrative embodiments of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method for instilling an ophthalmic agent, the method comprising:
    causing a patient to refrain from blinking for at least a period of time so as to initiate the break down of the patient's tear film covering the patient's eye; and thereafter instilling an ophthalmic agent to the patient's eye.

2. The method of claim 1, wherein the period of time is between about 2 seconds to about 30 seconds.

3. The method of claim 1, wherein the period of time is 6 seconds.

4. The method of claim 1 wherein the period of time is determined based on ocular discomfort associated with disruption of the patient's tear film.

5. The method of claim 1, wherein the ophthalmic agent is selected from the group of ophthalmic agents consisting of mydriatics and cycloplegics, antimicrobial therapy agents, ocular anti-inflammatory products, anesthetic products, products for treatment of glaucoma, products for dry eye, ocular decongestants, hyperosmolar products, diagnostic products, and viscoelastic materials used in ophthalmology.

6. The method of claim 2 wherein the ophthalmic agent is selected from the group of ophthalmic agents consisting of mydriatics and cycloplegics, antimicrobial therapy agents, ocular anti-inflammatory products, anesthetic products, products for treatment of glaucoma, products for dry eye, ocular decongestants, hyperosmolar products, diagnostic products, and viscoelastic materials used in ophthalmology.

7. The method of claim 3 wherein the ophthalmic agent is selected from the group of ophthalmic agents consisting of mydriatics and cycloplegics, antimicrobial therapy agents, ocular anti-inflammatory products, anesthetic products, products for treatment of glaucoma, products for dry eye, ocular decongestants, hyperosmolar products, diagnostic products, and viscoelastic materials used in ophthalmology.

8. The method of claim 4 wherein the ophthalmic agent is selected from the group of ophthalmic agents consisting of mydriatics and cycloplegics, antimicrobial therapy agents, ocular anti-inflammatory products, anesthetic products, products for treatment of glaucoma, products for dry eye, ocular decongestants, hyperosmolar products, diagnostic products, and viscoelastic materials used in ophthalmology.

\* \* \* \* \*